United States Patent [19]

Hakamatsuka et al.

[11] Patent Number: 4,770,943

[45] Date of Patent: Sep. 13, 1988

[54] METHOD OF FORMING RIGID FILM OF CALCIUM PHOSPHATE COMPOUND

[75] Inventors: Yasuharu Hakamatsuka, Tokyo; Sukezo Kawamura, Inuyama; Motohiro Toriyama, Nagoya, all of Japan

[73] Assignees: Olympus Optical Co., Ltd.; Director-General of Agency of Industrial Science and Technology, both of Tokyo, Japan

[21] Appl. No.: 123,221

[22] Filed: Nov. 20, 1987

[30] Foreign Application Priority Data

Nov. 25, 1986 [JP] Japan ................... 61-280160

[51] Int. Cl.$^4$ .................. B05D 1/36; B05D 3/02; B05D 7/00; B32B 9/00

[52] U.S. Cl. .................. 428/471; 427/380; 427/419.2; 427/419.6; 428/697; 428/699; 428/702

[58] Field of Search ............. 427/376.1, 380, 419.2, 427/419.5, 419.6; 428/471, 472.2, 472.3, 697, 699, 702

[56] References Cited

U.S. PATENT DOCUMENTS

| | | | |
|---|---|---|---|
| 4,108,690 | 8/1978 | Heller | 148/6.15 R |
| 4,539,051 | 9/1985 | Halias | 427/419.5 X |
| 4,582,725 | 4/1986 | Nakashima | 427/419.6 X |

FOREIGN PATENT DOCUMENTS

| | | |
|---|---|---|
| 62-87406 | 4/1987 | Japan . |
| 62-116781 | 5/1987 | Japan . |
| 62-162676 | 7/1987 | Japan . |
| 1232944 | 5/1971 | United Kingdom . |

*Primary Examiner*—Michael R. Lusignan
*Attorney, Agent, or Firm*—Frishauf, Holtz, Goodman & Woodward

[57] ABSTRACT

A method of forming a rigid film of calcium phosphate compound having good bio-conformance on a surface of a ceramic or metal substrate is disclosed. According to this method, a slurry of a fine powder of phosphate-series glass of $CaO-Na_2O-P_2O_5-Al_2O_3$ is applied to the surface of the substrate and is dried and heat-treated to form a binder layer which covers the surface of the substrate. A peptisation agent such as ammonium polyacrylate and water are mixed with a fine powder of a calcium phosphate compound having a particle size of 1 μm or less to prepare a slurry, and this slurry is applied to the surface of the binder layer. The slurry on the binder layer is dried and heat-treated to form a film of the calcium phosphate compound. The film of the calcium phosphate compound formed by this method is uniform and has high adhesion strength with the substrate.

10 Claims, No Drawings

METHOD OF FORMING RIGID FILM OF CALCIUM PHOSPHATE COMPOUND

BACKGROUND OF THE INVENTION

1. Field of the Invention

The present invention relates to a method of forming a rigid film of a calcium phosphate compound having good bio-conformance on a surface of a ceramic or metal substrate and, more particularly, to a method of forming the film by using a calcium phosphate compound slurry.

2. Description of the Prior Art

A single-crystal sapphire, a ceramic material (e.g., an alumina or zirconia sintered body) and a metal material (e.g., titanium, a titanium alloy, or a stainless steel) have high strength and are nontoxic to a living body. Such a material is used as an intracorporeal indwelling material such as an artificial dental root and an artificial bone. However, the material is inert with regard to the tissue of a living body and does not have a bonding capacity with a new bone. In addition, a wrapping phenomenon by a film of foreign matter tends to occur. As a result, the material cannot be embedded in a living body for a long period of time.

However, a calcium phosphate compound such as hydroxy apatite or tricalcium phosphate is a major constituent of the inorganic component in a living body such as a tooth and a bone and is not toxic to a living body. Therefore, the calcium phosphate compound has good bio-conformance such as a good bonding property with a bone and substitution with a new bone. However, a high strength sintered body of the calcium phosphate compound has never been proposed in practice.

In consideration of the above situation, a strong demand has arisen for an intracorporeal indwelling material having high strength and good bio-conformance. In order to meet such a demand, a composite material obtained by coating a calcium phosphate compound on a surface of a single-crystal sapphire, ceramic or metal material is most promising, and extensive studies on it have been made.

Conventional methods of forming a calcium phosphate compound film on a surface of an intracorporeal indwelling material are proposed as follows.

First, a calcium phosphate compound is melted by a high-temperature flame and sprayed at high speed on the surface of a substrate (spraying process).

Second, a calcium phosphate compound is sputtered on the surface of a substrate (sputtering method).

Third, a calcium phosphate compound slurry is applied to the surface of a substrate by spraying or dipping and is dried and sintered (slurry method).

Fourth, a chemical precipitation method proposed by the present applicant (Japanese Patent Disclosure (Kokai) No. 62-116781) is available.

The above conventional methods have both advantages and disadvantages. Improvements of these methods have been made. Of these conventional methods, the slurry method does not require special equipment and can be easily practiced at low cost. Therefore, the slurry method is most promising.

The slurry method, however, has disadvantages in that adhesion strength of the film with the substrate is low, and formation of a uniform film on the surface of the substrate is difficult due to the following reason. The particles of the calcium phosphate compound used to prepare a slurry have a large size of about 8 $\mu m$. When the particle size is large, a coagulation force is generated between the particles, and the particles cannot be uniformly dispersed in the slurry. Therefore, the slurry cannot be properly applied to projections or recesses of the substrate, resulting in a nonuniform film. In addition, good sintering of the substrate and the film cannot be performed. The resultant film is nonuniform, and the film tends to peel from the substrate due to a difference between the thermal expansion coefficients of the film and the substrate.

SUMMARY OF THE INVENTION

It is an object of the present invention to provide an economical method of forming a calcium phosphate compound film on a surface of a ceramic or metal substrate by improving the above-mentioned slurry method, thereby obtaining high adhesion strength between the substrate and the film and, at the same time, a uniform film.

In order to achieve the above object of the present invention, there is provided a method of forming a calcium phosphate compound film, comprising the steps of:

(a) mixing a peptisation agent such as an ammonium polyacrylate and water with a fine powder of a calcium phosphate compound having a particle size of 1 $\mu m$ or less to prepare a slurry;

(b) applying a phosphate glass powder slurry of $CaO-Na_2O-P_2O_5-Al_2O_3$ to a surface of a ceramic or metal substrate, and drying and heat-treating the phosphate glass powder slurry to form a binder layer which covers the surface of the ceramic or metal substrate; and (c) applying the calcium phosphate compound slurry to the binder layer, and drying and heat-treating the calcium phosphate compound slurry to form a calcium phosphate compound film.

DESCRIPTION OF THE PREFERRED EMBODIMENT

A method of the present invention differs from the conventional slurry method in the following two points.

First, a fine powder of a calcium phosphate compound having a particle size of 1 $\mu m$ or less is used to prepare a slurry. Such a fine powder can be prepared by a wet pulverization method (a so-called mechano-chemical method) with a mechano-chemical effect. The fine powder of the calcium phosphate compound prepared by this method can be suitably used in the present invention.

The mechano-chemical method was previously proposed by the present applicant (Japanese Patent Disclosure (Kokai) No. 62-87406 and Japanese Patent Application No. 61-30575). According to this method, $CaCO_3$, $CaHPO_4.2H_2O$, and water are mixed to prepare a slurry having a 10 wt% solid content. The slurry is pulverized mechano-chemically by using a wet ball mill for about 24 hours, and the components of the slurry are reacted with each other. The reacted slurry is dried at about 80° C. and presintered at 750° to 1,000° C. for an hour, thereby obtaining a fine powder of tricalcium phosphate or hydroxy apatite. The fine powder of tricalcium phosphate or hydroxy apatite is easily selected by controlling a ratio of $CaCO_3$ to $CaHPO_4.2H_2O$. The particle size of the fine powder obtained by the mechano-chemical method is 1 $\mu m$ or less and is 1/10 to 1/20 of the calcium phosphate compound particle used in the conventional slurry method.

The second difference between the method of the present invention and the conventional slurry method is as follows. A binder layer of $CaO-Na_2O-P_2O_5-Al_2O_3$ is formed between the substrate and the calcium phosphate compound film. The properties of this glass layer are similar to those of the calcium phosphate compound film formed by the present invention. The binder layer can improve adhesion strength and substantially reduces a difference of thermal expansion coefficients between the substrate and the calcium phosphate compound film, thereby preventing peeling of the film from the substrate. The binder layer can be formed by the slurry method. A slurry for the binder layer is formed such that a fine powder of $CaO-Na_2O-P_2O_5-Al_2O_3$ (to be referred to as a fine powder for binder hereinafter) is dispersed together with a proper peptisation agent in water.

Except for the above two points, the method of the present invention is the same as the conventional slurry method.

A ceramic sintered body of zirconia, alumina, zirconia-yttria series, or zirconia-alumina-yttria series, and so on is used as a substrate. A metal such as titanium, a titanium alloy, or stainless steel can also be used as a metal substrate.

A conventional peptisation agent such as ammonium polyacrylate or the like can be used to prepare the slurry. A known method such as spraying or dipping may be used as a method of applying a slurry to the substrate. The concentration of the slurry and a pull-up speed in dipping must be properly controlled according to other conditions.

EXAMPLE 1

A zirconia sintered body was prepared as a substrate. In order to easily form a binder layer, the zirconia sintered body was dipped in a hydrofluoric acid solution for 5 minutes to roughen the surface of the sintered body.

A fine powder for binder was added to a 10% ammonium polyacrylate aqueous solution and was mixed by ultrasonic vibrations to prepare a slurry. 10 g of the fine powder for binder were added to 40 cc of the ammonium polyacrylate aqueous solution. The resultant slurry was applied to a surface of the zirconia substrate to form a slurry layer having a thickness of about 2 μm. The slurry was dried and sintered at 1,000° C. for 30 minutes, thereby forming a binder layer closely adhered on the substrate.

A fine powder of β-tricalcium phosphate having a particle size of 0.4 μm or less and prepared by the mechano-chemical method was mixed with a 10% ammonium polyacrylate aqueous solution to prepare a slurry. In this case, 10 g of the fine powder of β-tricalcium phosphate were mixed with 40 cc of the ammonium polyacrylate aqueous solution. The resultant slurry was uniformly applied to the surface of the binder layer by a spray gun to form a slurry layer having a uniform thickness of about 3 μm. The applied slurry was dried at 20° to 40° C. Subsequently, the resultant structure was placed in a sintering furnace and heated at a rate of 100° to 300° C./hour. The structure was sintered at 1,100° C. for 30 minutes and was then cooled in the furnace, thereby forming a β-tricalcium phosphate film.

Adhesion strength of the formed film was measured by a scratch test, and high adhesion strength was obtained as compared with the conventional slurry method.

EXAMPLE 2

A film in Example 2 had a three-layered structure.

Following the same procedures as in Example 1, a binder layer was formed on a surface of a zirconia sintered body.

An intermediate layer was formed in the following manner. 3 g of a fine powder of β-tricalcium phosphate, 2 g of the binder powder, and 40 cc of a 10% ammonium polyacrylate aqueous solution were mixed to prepare a slurry. This slurry was sprayed by a spray gun and was dried.

A β-tricalcium phosphate slurry prepared following the same procedures as in Example 1 was sprayed by a spray gun and dried and sintered to form a β-tricalcium phosphate film.

Since the intermediate layer having an intermediate property between the β-tricalcium phosphate film and the binder layer was formed therebetween, a difference between the thermal expansion coefficients could be reduced. Therefore, the adhesion strength was higher than that in Example 1.

EXAMPLE 3

A titanium sintered body was used as a substrate. 3 g of a fine powder of hydroxy apatite, 2 g of the binder powder, and 40 cc of a 10% ammonium polyacrylate aqueous solution were mixed to prepare a slurry for an intermediate layer. The slurry for the intermediate layer in Example 3 was prepared such that the fine powder of β-tricalcium phosphate in the slurry of Example 2 was replaced with the fine powder of hydroxy apatite. Following the same procedures as in Example 2 except for the above two points, a three-layered film was formed on the surface of the substrate.

The film in Example 3 had the following advantages over those in Examples 1 and 2. Since β-tricalcium phosphate has good bio-conformance and can be easily replaced with a new bone, it can be absorbed in the living body and converted into a bone. As a result, the substrate bonded to tissue such as a bone through the β-tricalcium phosphate film is brought into direct contact with the tissue. Since a difference between the thermal expansion coefficients of the bone and the substrate is large, a crack may occur over a long period of time. However, since a hydroxy apatite film is formed as the intermediate layer, hydroxy apatite is easily bonded to the tissue of a living body but tends not to be absorbed in the tissue of the living body. Therefore, the entire film is not absorbed in the tissue of the living body and direct contact between the substrate and the tissue can be prevented. Therefore, the sample in Example 3 is suitable for long-term indwelling.

What is claimed is:

1. A method of forming a calcium phosphate compound film, comprising the steps of:
   (a) mixing a peptisation agent and water with a fine powder of a calcium phosphate compound having a particle size of 1 μm or less to prepare a slurry;
   (b) applying a phosphate glass powder slurry of $CaO-Na_2O-P_2O_5-Al_2O_3$ to a surface of a ceramic or metal substrate, and drying and heat-treating the phosphate glass powder slurry to form a binder layer which covers the surface of the ceramic or metal substrate; and (c) applying the calcium phosphate compound slurry to the binder layer, and drying and heat-treating the calcium phosphate compound slurry to form a calcium phosphate compound film.

2. A method according to claim 1, wherein the fine powder of the calcium phosphate compound is prepared by a wet pulverization method with a mechano-chemical effect.

3. A method according to claim 2, wherein the wet pulverization method is such that $CaCO_3$, $CaHPO_4.2H_2O$, and water are mixed to prepare a slurry, the slurry is mechano-chemically pulverized and reacted by a wet ball mill, and is dried and presintered.

4. A method according to claim 1, wherein the calcium phosphate compound is tricalcium phosphate.

5. A method according to claim 4, wherein the tricalcium phosphate is $\beta$-tricalcium phosphate.

6. A method according to claim 4, wherein the tricalcium phosphate is $\alpha$-tricalcium phosphate.

7. A method according to claim 1, wherein the calcium phosphate compound is hydroxy apatite.

8. A method according to claim 1, further comprising the step of:
applying a slurry containing a fine powder of phosphate-series glass of $CaO-Na_2O-P_2O_5-Al_2O_3$ and the fine powder of the calcium phosphate compound and drying the slurry to form an intermediate layer after step (b) and before step (c).

9. A living body indwelling member prepared such that a film of a calcium phosphate compound is formed on a surface of a ceramic or metal substrate according to the method of claim 1.

10. A method according to claim 1 wherein the peptizing agent is ammonium acrylate.

* * * * *